US012295875B2

(12) United States Patent
Holroyd et al.

(10) Patent No.: US 12,295,875 B2
(45) Date of Patent: May 13, 2025

(54) OSTOMY APPLIANCE COUPLING ASSEMBLY

(71) Applicant: CONVATEC LIMITED, Flintshire (GB)

(72) Inventors: Simon Holroyd, London (GB); Dominic Baker, London (GB); Stefan Taal, London (GB); Marko Plevnik, London (GB)

(73) Assignee: CONVATEC LIMITED, Flintshire (GB)

( * ) Notice: Subject to any disclaimer, the term of this patent is extended or adjusted under 35 U.S.C. 154(b) by 776 days.

(21) Appl. No.: 17/179,691

(22) Filed: Feb. 19, 2021

(65) Prior Publication Data

US 2021/0259875 A1   Aug. 26, 2021

Related U.S. Application Data

(63) Continuation of application No. PCT/GB2021/050409, filed on Feb. 19, 2021.

(30) Foreign Application Priority Data

Feb. 20, 2020 (GB) ..................................... 2002380
Feb. 20, 2020 (GB) ..................................... 2002388

(51) Int. Cl.
    *A61F 5/448* (2006.01)
(52) U.S. Cl.
    CPC ...... *A61F 5/448* (2013.01); *A61F 2005/4486* (2013.01)
(58) Field of Classification Search
    CPC .. A61F 5/448; A61F 2005/4486; A61F 5/445; A61F 2005/4483; A61F 2005/4455;
    (Continued)

(56) References Cited

U.S. PATENT DOCUMENTS 3,074,404 A   1/1963  Robinson
3,789,846 A   2/1974  Barrett et al.
              (Continued)

FOREIGN PATENT DOCUMENTS

DE   3741207 C2 *  4/1996  ............. A61F 5/448
EP    381393 A  *  8/1990  ............. A61F 5/448
              (Continued)

OTHER PUBLICATIONS

Mohiuddin, Schneider, O Kay, Auxiliary Device for Artificial Body Openings, 1987, Google Patents Translation (Year: 1987).*

(Continued)

*Primary Examiner* — Philip R Wiest
*Assistant Examiner* — Brandon W. Levy
(74) *Attorney, Agent, or Firm* — TAFT STETTINIUS HOLLISTER LLP; Ryan O. White; Derek B. Lavender

(57) ABSTRACT

A coupling assembly for an ostomy appliance that has a locking arrangement, a first coupling and a second coupling. The locking arrangement has a locking ring and first and second grips mounted to the locking ring. The locking ring is mounted to first and/or second coupling, forms an inner circumference and is adjustable between locked and unlocked configurations. In the locked configuration the locking ring is for maintaining the first and second couplings in a coupled configuration and the inner circumference is less than in the unlocked configuration. The first and second grips are positioned about the locking ring to be moveable towards one another to increase the inner circumference and adjust the locking ring from the locked configuration to the unlocked configuration.

20 Claims, 8 Drawing Sheets

(58) Field of Classification Search
CPC .............. A61F 2005/4402; A61F 5/443; A61F 5/4407; A61F 5/4404; A61F 5/4405; A61F 5/449; A61F 13/5616; A61F 13/42; A61F 13/00051; A61F 13/0246; A61F 2013/424; A44D 2203/00; B65D 33/24; B65D 35/44; A61L 28/00; Y10T 24/15; A61B 5/6811; A61B 5/746; B32B 2535/00; G01N 27/223; G16H 40/67; G01M 3/16

See application file for complete search history.

(56) References Cited

U.S. PATENT DOCUMENTS

| | | | |
|---|---|---|---|
| 4,889,534 | A | 12/1989 | Mohiuddin et al. |
| 4,917,591 | A | 4/1990 | Sakaida et al. |
| 5,026,360 | A * | 6/1991 | Johnsen ............... A61F 5/448 604/338 |
| 5,322,522 | A * | 6/1994 | Olsen ................. A61F 5/448 604/338 |
| 5,364,379 | A | 11/1994 | Ozenne et al. |
| 5,496,297 | A | 3/1996 | Olsen |
| 5,647,861 | A * | 7/1997 | Steer ................. C07C 43/11 604/338 |
| 5,957,905 | A | 9/1999 | Steer |
| 7,496,994 | B1 | 3/2009 | Headley |
| 11,065,144 | B2 | 7/2021 | Nielsen et al. |
| 11,083,617 | B2 | 8/2021 | Larsen |
| 11,298,257 | B2 | 4/2022 | Fernandez et al. |
| 11,737,906 | B2 | 8/2023 | Jones |
| 11,890,219 | B2 | 2/2024 | Schoess et al. |
| 2009/0118687 | A1* | 5/2009 | Kristensen ............ A61F 5/448 604/342 |
| 2015/0045755 | A1* | 2/2015 | Pedersen ............. A61F 5/448 604/342 |
| 2021/0244497 | A1 | 8/2021 | Taweh |
| 2021/0259875 | A1 | 8/2021 | Holroyd et al. |
| 2024/0000601 | A1 | 1/2024 | Jones, Jr. |

FOREIGN PATENT DOCUMENTS

| | | | |
|---|---|---|---|
| EP | 737456 | A2 | 10/1996 |
| EP | 1008313 | A2 | 6/2000 |
| EP | 1008313 | A3 | 9/2001 |
| EP | 3410993 | B1 | 6/2021 |
| EP | 2846746 | B1 | 3/2022 |
| GB | 1212904 | A | 11/1970 |
| GB | 2201346 | A * | 9/1988 ............ A61F 5/448 |
| GB | 2261376 | A | 5/1993 |
| JP | 2010273988 | A | 12/2010 |
| WO | 199101118 | A1 | 2/1991 |
| WO | 2007059774 | A2 | 5/2007 |
| WO | 2013131523 | A1 | 9/2013 |

OTHER PUBLICATIONS

Partial Search, European Patent Office, International Patent Application No. PCT/GB2020/053258, 4 pages.
Invitation to Pay Additional Fees, European Patent Office, International Patent Application No. PCT/GB2020/053258, Mar. 19, 2021, 8 pages.
International Search Report; European Patent Office; International Application No. PCT/GB2021/050409; May 31, 2021; 3 pages.
Written Opinion of the International Searching Authority; European Patent Office; International Application No. PCT/GB2021/050409; May 31, 2021; 6 pages.
Notice of Opposition for European Patent No. EP4106693; 41 pages.
Office Action for JP2022-549963; 2 pages.

* cited by examiner

OSTOMY APPLIANCE COUPLING ASSEMBLY

CROSS-REFERENCE TO RELATED APPLICATIONS

This application is a continuation of International Application No. PCT/GB2021/050409 filed Feb. 19, 2021 and claims the priority of foreign Application Nos. GB2002380.0 and GB2002388.3, each filed Feb. 20, 2020. The disclosures of which are hereby incorporated herein in their entirety.

TECHNICAL FIELD

The present disclosure relates to a coupling assembly for an ostomy appliance and an ostomy appliance comprising such a coupling assembly.

BACKGROUND OF THE DISCLOSURE

There are many forms of ostomy appliances which aim to provide a secure, comfortable fit for ostomates. Ostomy appliances commonly comprise a pouch for collecting stomal output and are commonly attached to the body by means of a wafer, often via at least one adhesive layer on the wafer. The wafer extends around the stoma of the ostomate. In a "two-piece appliance" a coupling assembly is provided to enable the wafer to be releasably attached to the pouch. A two-piece appliance permits the wafer to be separated from the pouch without damage, so that at least one of the components continues to be functionally usable. For example, the wafer may remain in place on the body of the ostomate whilst the pouch may be replaced.

EP-A-0737456 discloses a coupling assembly for a two-piece appliance having first and second coupling members. These can be held together by a springy flexible split locking ring. A plurality of tabs, arranged on to limbs of the locking ring, can be withdrawn generally radially outwardly by movement of the locking ring to permit separation of the two coupling members. The movement of the locking ring which causes withdrawal of the tabs is a rotational movement relative to the second coupling member. The locking ring may be effective in holding the first and second coupling members together and preventing unintended uncoupling. However, the rotational movement may result in the transfer, via the coupling assembly and wafer, of a torque to the area of the body surrounding the stoma. This may cause discomfort for the ostomate.

GB-A-2323286 discloses a coupling assembly for a two-piece appliance comprising first and second coupling members and a mechanical locking ring for releasably securing the coupling members together. A deflectable or compressible sealing member on one of the coupling members deflects or compresses in a generally axial direction to produce a generally axial sealing force. Again, however, rotation of the locking ring may cause a transfer of torque to the body of the ostomate and thus cause discomfort. In addition, stomal output may enter the area between the first and second coupling members such that the coupling arrangement is harder to clean and effective sealing between the existing wafer and a new replacement pouch may become harder to achieve.

SUMMARY OF THE DISCLOSURE

In this specification, the term "stomal output" refers to any gases or fluids or solids produced by an ostomate that may be secreted from the stoma or that exit the stoma. The stomal output may comprise stomal gas, stomal liquid and stomal solids.

In this specification, the term "stoma" refers to an opening in the body. Generally the stoma is a surgical opening in the torso of the body. In some instances, the term "stoma" also refers to internal tissue, organs or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

In this specification, the term "ostomate" refers to a subject that may have use of the belt mount for an ostomy appliance disclosed herein. While ostomate usually refers to a subject with a surgical opening, as used herein, "ostomate" may refer to a subject who has a stoma, regardless of whether the stoma was created by surgery or other means. The term "user" may refer to an ostomate, or to another person assisting the ostomate, for example, with emptying of the stomal output from the cavity.

In this specification, the ostomy appliances disclosed herein may, for example, be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, a urostomy, a nephrostomy, an ureterostomy, or a vesicostomy. The ostomy appliances disclosed herein may be used with additional devices including, but not limited to, a shunt, a catheter, a plug or a fecal management system.

In this specification locations and orientations of features may be described with reference to the belt mount for an ostomy appliance being "in use", "orientated as it would be in use" or similar. Such terms refer to the intended orientation of the belt mount for an ostomy appliance when it is secured to a body of an ostomate with the ostomate in a standing position, irrespective of whether the ostomy appliance is currently performing such a use or the actual position of the ostomate. In particular, the terms "top" and "bottom" may refer to those locations of the ostomy appliance or the components thereof when in use.

In this specification, the wafer may be for attachment to the body of ostomate around a stoma for attaching the ostomy appliance to the ostomate. The term "wafer" may be used interchangeably with the terms "adapter," "ostomy wafer," "baseplate", or "layered adhesive wafer". The wafer may comprise at least one adhesive layer on a body-facing side for adhering the wafer to the body of the ostomate. A release liner may cover a body-facing side of the wafer that is removed by the user prior to fitting to the skin. The wafer may comprise additional features such as a belt mount.

In this specification, the term "pouch" may be used interchangeably with the term "bag" and may comprise at least one film defining a cavity for collecting stomal output. The pouch may comprise at least one filter for separating stomal solids from stomal liquid and/or gas. The pouch may comprise at least one drain for selectively draining the stomal output from the pouch.

The present disclosure therefore provides a coupling assembly for an ostomy appliance comprising a locking arrangement, a first coupling and a second coupling, wherein the locking arrangement comprises: a locking ring, mounted to first and/or second coupling, forming an inner circumference and being adjustable between locked and unlocked configurations, wherein in the locked configuration the locking ring is for maintaining the first and second couplings in a coupled configuration and the inner circumference is less than in the unlocked configuration; and first and second grips mounted to the locking ring, wherein the first and second grips are positioned about the locking ring to be moveable towards one another to increase the inner circumference and adjust the locking ring from the locked configuration to the unlocked configuration.

As the first and second grips are moveable towards one another during unlocking, a substantial rotational torque is not transferred from the coupling assembly to a wafer attached thereto during unlocking. As a result, the locking arrangement improves the comfort of the ostomate.

The locking ring may be springy and resiliently biased to return from the unlocked configuration to the locked configuration. The locking ring may comprise first and second locking ring ends moveable relative to one another between the locked and unlocked configurations. The locking ring may be split.

The locking ring may extend around a length that is greater than the inner circumference in the locked configuration. The distance between the first and second grips around the length of the locking ring may be greater than the inner circumference in the locked configuration.

The coupling assembly may further comprise first and second pinch tabs extending from the locking ring and comprising the first and second grips respectively. The first and second pinch tabs may slide adjacent to one another when the locking ring is adjusted between the locked and unlocked configurations.

The first pinch tab may extend around the locking ring between a first tab distal end and a first tab proximal end. The second pinch tab may extend around the locking ring between a second tab distal end and a second tab proximal end. The first and second tab distal ends may form the first and second grips. In the locked configuration the first and second tab distal ends may be aligned with the second and first tab proximal ends respectively. The first and second pinch tabs may comprise first and second tab proximal portions adjacent to the locking ring forming the first and second tab proximal ends and first and second tab distal portions extending radially outwardly from the first and second tab proximal portions forming the first and second tab distal ends. The first and second tab distal portions may extend around the locking ring between the first and second tab distal ends and first and second tab inner edges. In the unlocked configuration the first and second tab distal ends may be aligned with the second and first tab inner edges respectively.

The locking ring may comprise at least one locking tab extending inwardly around the inner circumference for maintaining the coupling assembly in the coupled configuration when the locking ring is in the locked configuration. The locking ring may be mounted to the first coupling and the at least one locking tab may be configured to engage with the second coupling when in the coupled and locked configurations to maintain the first and second couplings in the coupled configuration.

The first coupling may comprise at least one first coupling opening. The at least one locking tab may be configured to engage the second coupling through the at least one first coupling opening when in the coupled and locked configurations to maintain the first and second couplings in the coupled configuration.

The second coupling may comprise a second coupling outer flange. The at least one locking tab may be configured to at least partially overlap the second coupling outer flange when in the coupled and locked configurations to maintain the first and second couplings in the coupled configuration.

The coupling assembly may comprise a first and/or second grip constraining arrangement configured to constrain radial and/or circumferential movement of the first and second grips when the locking ring is adjusted between the locked and unlocked configurations. The first grip constraining arrangement may comprise at least one constraining pin slidably mounted in at least one constraining slot. The at least one constraining slot may be formed in at least one of the locking ring, first pinch tab and second pinch tab and the at least one constraining pin may be attached to the first coupling or vice-versa. The second grip constraining arrangement may comprise a radially extending constraining protrusion mounted in at least one radially extending constraining recess. The first coupling may comprise the constraining protrusion and the locking ring may comprise the at least one constraining recess or vice-versa.

The coupling assembly may comprise a centring arrangement configured to constrain circumferential movement of at least a portion of the locking ring when the locking ring is adjusted between the locked and unlocked configurations. The centring arrangement may comprise at least one centring protrusion mounted in at least one centring recess. The first coupling may comprise the at least one centring protrusion and the locking ring may comprise the at least one centring recess or vice-versa.

The coupling assembly may comprise a sealing arrangement extending around a coupling aperture, the sealing arrangement being located between the first and second couplings in the coupled configuration, wherein in the coupled configuration the sealing arrangement is compressed along the axial direction to form a seal between the first and second couplings and the sealing arrangement is located adjacent to and at least partially bounds the coupling aperture.

The present disclosure further provides a coupling assembly for an ostomy appliance comprising a first coupling, a second coupling and a sealing arrangement extending around a coupling aperture, the first and second couplings being coupleable together along an axial direction into a coupled configuration and the sealing arrangement being located between the first and second couplings, wherein in the coupled configuration the sealing arrangement is compressed along the axial direction to form a seal between the first and second couplings and the sealing arrangement is located adjacent to and at least partially bounds the coupling aperture.

The sealing arrangement may therefore be positioned such that it prevents stomal output from entering in between the first and second couplings. As a result, the first and second couplings may not be contaminated by the stomal output such that the first and second couplings may remain cleaner to enable effective coupling and sealing therebetween.

The coupling aperture may be bounded by the first coupling, the second coupling and the sealing arrangement. In particular the coupling aperture may be formed by the first and second coupling and sealing arrangement and/or the first and second coupling and sealing arrangement may all be exposed at the coupling aperture.

The first coupling may comprise a first coupling inner wall and a first coupling channel extending around the first coupling inner wall. The second coupling may comprise a second coupling wall and a second coupling inner flange extending radially inwardly towards the coupling aperture from the second coupling wall. The first and second couplings may be coupleable together into a coupled configuration in which the second coupling wall extends into the first coupling channel, the second coupling inner flange extends over the first coupling inner wall and the sealing arrangement is formed between the second coupling inner flange and first coupling inner wall.

The present disclosure further provides a coupling assembly for an ostomy appliance comprising first and second couplings extending around a coupling aperture and a sealing arrangement for sealing the first and second couplings together, wherein: the first coupling comprises a first coupling inner wall and a first coupling channel extending around the first coupling inner wall; the second coupling comprises a second coupling wall and a second coupling inner flange extending radially inwardly towards the coupling aperture from the second coupling wall; and the first and second couplings are coupleable together into a coupled configuration in which the second coupling wall extends into the first coupling channel, the second coupling inner flange extends over the first coupling inner wall and the sealing arrangement is formed between the second coupling inner flange and first coupling inner wall.

The sealing arrangement may therefore be positioned such that it prevents stomal output from entering the first coupling channel. As a result, the first coupling channel may not be contaminated by the stomal output such that the first and second couplings may remain cleaner to enable effective coupling and sealing therebetween.

The first coupling may comprise a first coupling outer wall extending around the first coupling channel. The first and second couplings may extend circumferentially around the coupling aperture. The first coupling inner wall and channel may extend circumferentially. The second coupling wall and inner flange may extend circumferentially. The second coupling may comprise a second coupling outer flange extending radially outwardly away from the coupling aperture from the second coupling wall. In the coupled configuration the second coupling outer flange may extend radially outwardly in the first coupling channel.

The sealing arrangement may comprise a resiliently deformable material. The sealing arrangement may comprise the second coupling inner flange and/or the first coupling inner wall. At least part of the second coupling inner flange and/or first coupling inner wall may comprise the resiliently deformable material.

The sealing arrangement may comprise a seal element mounted between the second coupling inner flange and first coupling inner wall. The seal element may be attached to the second coupling. The seal element may comprise a closed ring.

The coupling assembly of the present disclosure may comprise any combination of the features disclosed herein. Thus the coupling assembly with the locking arrangement may comprise a sealing arrangement for sealing the first and second couplings together. The coupling assembly with the sealing arrangement may comprise a locking arrangement for locking the first and second couplings together in the coupled configuration. The at least one locking tab may be configured to selectively overlap the second coupling outer flange to hold the first and second coupling in the coupled configuration. The first coupling outer wall may comprise at least one first coupling opening for receiving the at least one locking tab such that the at least one locking tab is configured to extend through the at least one first coupling opening and over the second coupling outer flange in the coupled configuration.

The first and second couplings may be for mounting to a wafer and a pouch of the ostomy appliance respectively or vice-versa. The present disclosure therefore further provides an ostomy appliance comprising the aforementioned coupling assembly, a pouch and a wafer, wherein the first coupling is attached to the wafer and the second coupling is attached to the pouch or vice-versa such that the wafer and pouch can be disconnected by uncoupling the first and second couplings.

BRIEF DESCRIPTION OF THE DRAWINGS

One or more embodiments of the disclosure will now be described, by way of example only, with reference to the accompanying drawings in which.

DETAILED DESCRIPTION OF THE DISCLOSURE

Figure 1:
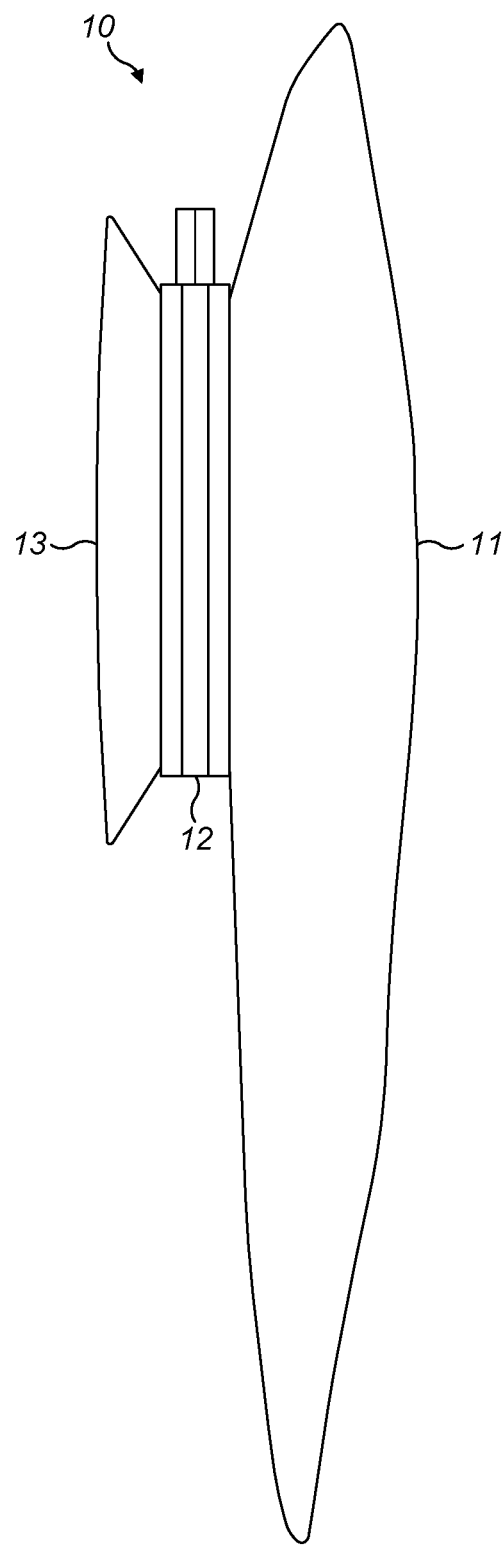
FIG. 1 is a schematic side view of an embodiment of an ostomy appliance comprising a coupling assembly in accordance with the present disclosure.

In the following description, the equivalent reference numerals are used in different embodiments to denote equivalent or similar features. Unless defined otherwise, all technical and scientific terms used in this specification have the same meaning as is commonly understood by the reader skilled in the art to which the claimed subject matter belongs. It is to be understood that the foregoing summary of the disclosure and the following examples are exemplary and explanatory only and are not restrictive of any subject matter claimed.

The following description is directed to embodiments of the disclosure. The description of the embodiments is not meant to include all the possible embodiments of the disclosure that are claimed in the appended claims. Many modifications, improvements and equivalents which are not explicitly recited in the following embodiments may fall within the scope of the appended claims. Features described as part of one embodiment may be combined with features of one or more other embodiments unless the context clearly requires otherwise.

It is to be understood that at least some of the figures and descriptions of the disclosure have been simplified to focus on elements that are relevant for a clear understanding of the disclosure, while eliminating, for purposes of clarity, other elements that the reader skilled in the art will appreciate may also be required. Because such elements are well known to the reader skilled in the art, and because they do not necessarily facilitate a better understanding of the disclosure, a description of such elements is not provided herein.

In this specification, the use of the singular includes the plural unless the context clearly dictates otherwise. In this application, the use of "or" means "and/or" unless stated otherwise.

FIG. 1 illustrates an ostomy appliance 10 in accordance with the present disclosure comprising a pouch 11 for receiving and storing stomal output and releasably attached by a coupling assembly 12 to a wafer 13. The ostomy appliance 10 of the present disclosure may be a two-piece appliance.

Figure 2:
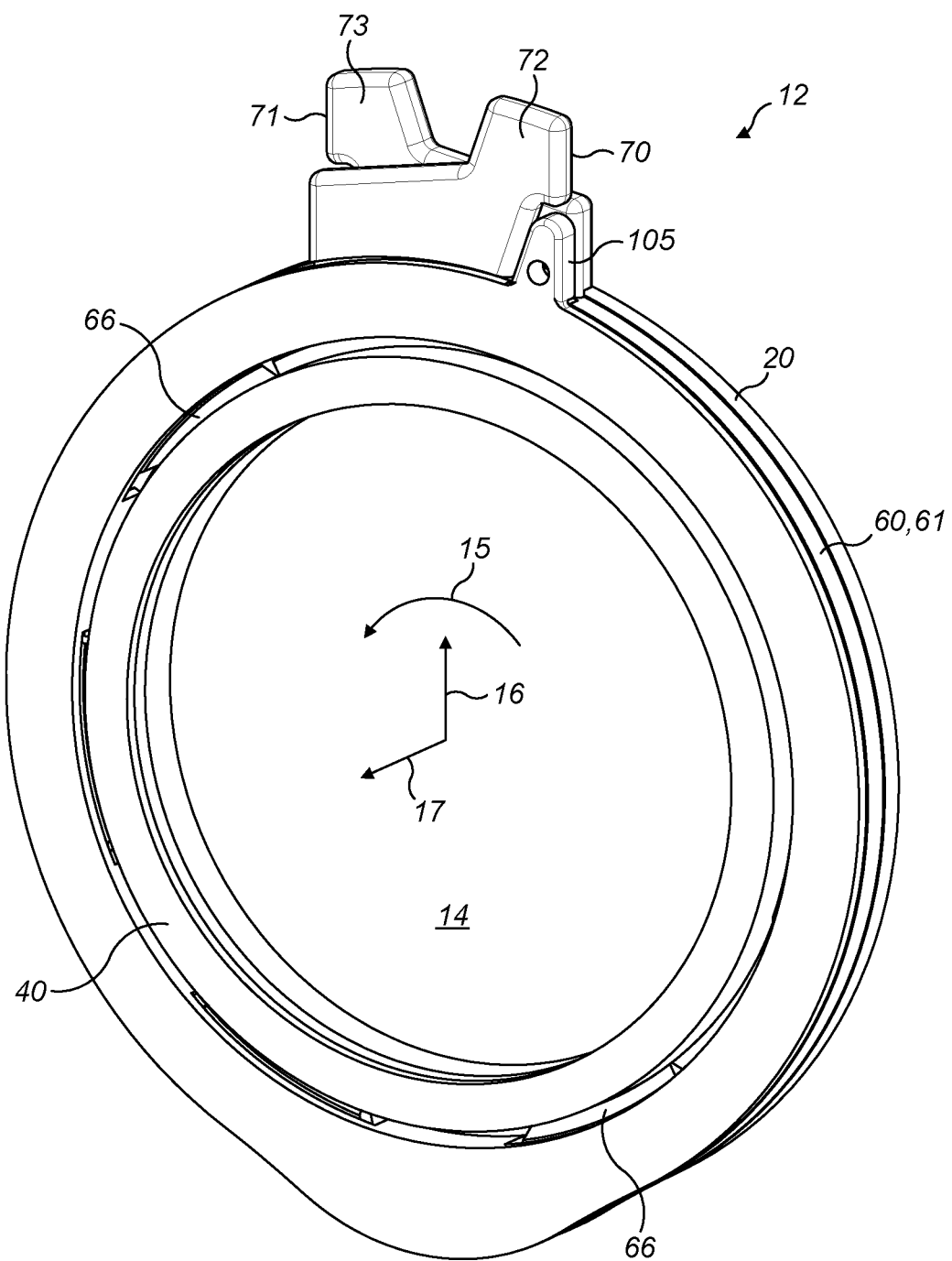
FIG. 2 is a perspective view of the coupling assembly of FIG. 1 in a coupled configuration.
Figure 3:
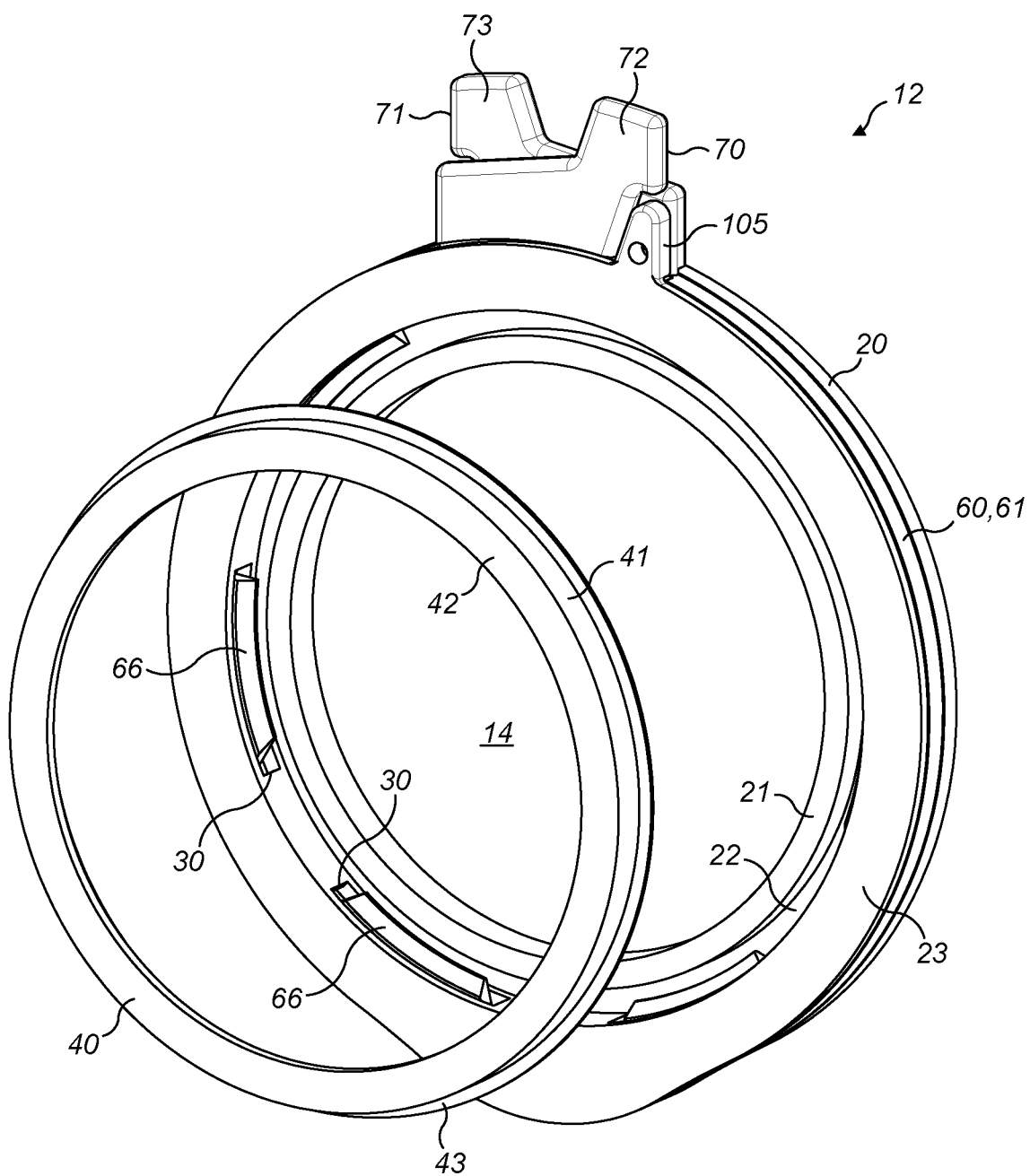
FIG. 3 is a perspective view of the coupling assembly of FIG. 1 in an uncoupled configuration.

As further illustrated in FIGS. 2 to 14, the coupling assembly 12 comprises a first coupling 20, a second coupling 40 and a locking arrangement 60, which may be moveable relative to one another. The coupling assembly 12 is configurable between a coupled configuration (as illustrated in FIGS. 1, 2 and 5) and an uncoupled configuration (as illustrated in FIG. 3). In the coupled configuration the ostomy appliance 10 is suitable for use on the ostomate by collecting stomal output and the first and second couplings 20, 40 are coupled or mounted together. In the uncoupled configuration the first and second couplings 20, 40 are uncoupled or separated from each other such that the wafer 13 and/or pouch 11 can be replaced.

In the following example the pouch 11 is mounted to the second coupling 40 and the wafer 13 is mounted to the first coupling 20. The first and second couplings 20, 40 may be uncoupled to separate the pouch 11 from the wafer 13, such as if the pouch 11 is replaced whilst the wafer 13 remains attached to the ostomate's body. However, in other embodiments the pouch 11 may instead be mounted to the first coupling 20 and the wafer 13 may be mounted to the second coupling 40. Additional elements may be mounted between the pouch 11, wafer 13 and first and/or second coupling 20, 40, but generally the uncoupling of the first and second couplings 20, 40 results in the pouch 11 being disconnected and separated from the wafer 13.

The first coupling 20 and second coupling 40 may extend around and define a coupling aperture 14, which may be for stomal output to pass through. The stomal output may therefore pass from the stoma, through a wafer aperture (not illustrated), through the coupling aperture 14, through a pouch aperture (not illustrated) and into the pouch 11.

The coupling assembly 12, first coupling 20, second coupling 40 and/or locking arrangement 60 may be substantially annular and/or may comprise open or closed rings. The coupling assembly 12, first coupling 20, second coupling 40 and/or locking arrangement 60 may comprise substantially circular annuli as illustrated, although the annuli may have another elliptical shape, such as oval or the like, or a polygonal shape, such as octagonal or the like.

Components of the present disclosure, particularly the coupling assembly 12, first coupling 20, second coupling 40 and/or locking arrangement 60, may extend:
  circumferentially around the coupling aperture 14, which may be a circumferential direction 15 around the outer perimeter of the coupling aperture 14 and stoma;
  radially from the coupling aperture 14, which may be an outward radial direction 16 from the centre of the coupling aperture 14 and stoma, which may be substantially along the ostomate's body; and/or
  axially, which may be an axial direction 17 through the coupling aperture 14 perpendicular to the circumferential and radial directions.

Components of the present disclosure, particularly the coupling assembly 12, first coupling 20, second coupling 40 and/or locking arrangement 60, may have:
  a length, which may be their dimension in the circumferential direction 15 around the coupling aperture 14;
  an outer width, which may be their maximum outer dimension in the radial direction 16;
  a breadth, which may be their dimension in the radial direction 16 from their inner perimeter to their outer perimeter (i.e. the breadth of the annulus); and/or
  a thickness, which may be their dimension in the axial direction 17.

The first coupling 20 is illustrated in further detail in FIGS. 3 to 8 and may comprise a first coupling inner wall 21 and a first coupling channel 22 extending around the first coupling inner wall 21. The first coupling channel 22 may be configured to receive at least part of the second coupling 40 in the coupled configuration. The first coupling 20 may comprise a first coupling outer wall 23 extending around the first coupling channel 22. A first coupling flange 24 may extend radially between the first coupling inner and outer walls 21, 23 such that the first coupling channel 22 may be formed therebetween. The first coupling inner and outer walls 21, 23 may extend in the same axial direction 17 from the first coupling flange 24 and the first coupling 20 may have a substantially U-shaped cross-section (i.e. across its breadth).

The first coupling inner wall, channel, outer wall and flange 21, 22, 23, 24 may extend circumferentially around the coupling aperture 14, preferably entirely around the coupling aperture 14 such that the first coupling 20 comprises a closed ring as illustrated. The first coupling inner wall 22 may extend substantially axially adjacent to the coupling aperture 14 and its thickness may be greater than its breadth. The breadth of the first coupling flange 24 may be greater than its thickness. The thickness, and optionally the breadth, of the first coupling outer wall 23 may be greater than that of the first coupling inner wall 21.

The first coupling 20 may comprise a first coupling slot 25 extending circumferentially around and radially inwardly from its outer perimeter. The first coupling slot 25 may be configured to receive at least part of the locking arrangement 60. The first coupling outer wall 23 may form the outer perimeter of the first coupling 20 and the first coupling slot 25 may extend circumferentially around and radially inwardly into the first coupling outer wall 23. The first coupling slot 25 may extend from the outer perimeter between first coupling slot walls 26, 27 to a first coupling slot base 28, each of which may be formed in and by the first coupling outer wall 23.

The first coupling 20 may comprise at least one first coupling opening 30 configured to receive at least part of the locking arrangement 60, as discussed further below. The at least one first coupling opening 30 may extend radially through the first coupling outer wall 23, preferably through the first coupling slot base 28, to the first coupling channel 22. The at least one first coupling opening 30 may be circumferentially elongate such that its length is greater than its thickness. The first coupling 20 preferably comprises at least four first coupling openings 30 and may comprise six as illustrated.

Figure 9:
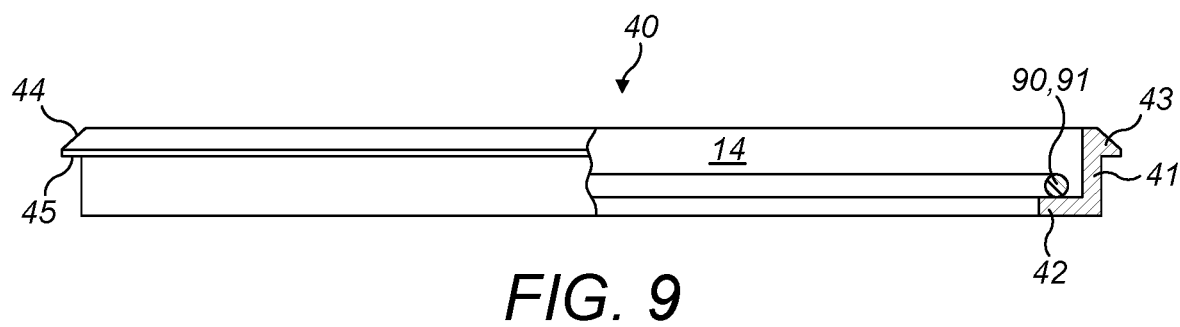
FIG. 9 is a partial cross-section side view of a second coupling of the coupling assembly of FIG. 1.

The second coupling 40 is illustrated in further detail in FIGS. 3, 5 and 9 and may comprise a second coupling wall 41 and may comprise a second coupling inner flange 42 extending radially inwardly towards the coupling aperture 14 from the second coupling wall 41. The second coupling 40 may comprise a second coupling outer flange 43, which may extend radially outwardly from the coupling aperture 14 from the second coupling wall 41. The second coupling inner and outer flanges 42, 43 may extend from axially opposite ends of the second coupling wall 41. The second coupling 40 may have a substantially Z-shaped cross-section (i.e. across its breadth).

The second coupling wall, inner flange and/or outer flange 41, 42, 43 may extend circumferentially around the coupling aperture 14, preferably entirely around the coupling aperture 14 such that the second coupling 40 comprises a closed ring as illustrated. The second coupling inner flange 42 may be adjacent to the coupling aperture 14 and its breadth may be greater than its thickness. The second coupling wall 41 may extend substantially axially such that its thickness may be greater than its breadth. The second coupling outer flange 43 may comprise a second coupling chamfered edge 44 facing outwardly from the second coupling wall 41 and/or a substantially second coupling flat edge 45 perpendicular to the outer surface of the second coupling wall 41.

In the coupled configuration, as illustrated in FIGS. 2 and 5, the first coupling 20 may be mounted to the second coupling 40 by the second coupling wall 41 being at least partially located in and extending into the first coupling channel 22. The second coupling wall 41 may be located between the first coupling inner and outer walls 21, 23. The second coupling inner flange 42 may extend over the first coupling inner wall 21, which may together form and define the coupling aperture 14. The second coupling wall 41 may be located adjacent to the first coupling inner wall 21. The second coupling outer flange 43 may be located adjacent to the first coupling outer wall 23 and may extend radially outwardly in the first coupling channel 22.

The coupling assembly 12 may further comprise a sealing arrangement 90 for sealing the first and second couplings 20, 40 together when in the coupled configuration. In particular, the first and second couplings 20, 40 may coupleable together along the axial direction 17 into the coupled configuration. The sealing arrangement 90 may be located between the first and second couplings 20, 40 and may be compressed along the axial direction 17 to form a seal between the first and second couplings 20, 40 in the coupled configuration. The sealing arrangement 90 is may be located adjacent to and at least partially bound the coupling aperture 14 such that it is directly exposed to the coupling aperture 14 and thus any stomal output passing therethrough.

The sealing arrangement 90 may be formed between the second coupling inner flange 42 and the first coupling inner wall 21. As a result, stomal output passing through the coupling aperture 14 may be immediately prevented by the sealing arrangement 90 from entering the interface between the second coupling inner flange 42 and the first coupling inner wall 21. The first coupling channel 22 may therefore be kept clean such that effective coupling and sealing can be maintained when the pouch 11 is replaced and a new second coupling 40 is coupled with the remaining first coupling 20.

The sealing arrangement 90 may comprise a resiliently deformable material that is compressed in the coupled configuration to form the seal. The sealing arrangement 90 may comprise, as illustrated, a separate seal element 91 mounted between the second coupling inner flange 42 and the first coupling inner wall 21. The seal element 91 may be attached to the second coupling 40 and preferably to the second coupling inner flange 42. The seal element 91 may be substantially annular and may comprise a closed ring, preferably an O-ring. Alternative or in addition, at least part of the second coupling inner flange 42 and/or the first coupling inner wall 21 may comprise the resiliently deformable material such that the sealing arrangement 90 comprises the second coupling inner flange 42 and/or the first coupling inner wall 21.

The locking arrangement 60 is for locking the first and second couplings 20, 40 together in the coupled configuration. As illustrated in further detail in FIGS. 4 and 10 to 14, the locking arrangement 60 comprises a locking ring 61 mounted around and to the first and/or second coupling 20, 40. In particular, the locking ring 61 may be mounted to the first coupling 40 and may be mounted in and extend around its first coupling slot 25. The locking ring 61 may be annular and extend circumferentially as illustrated.

Figure 14:
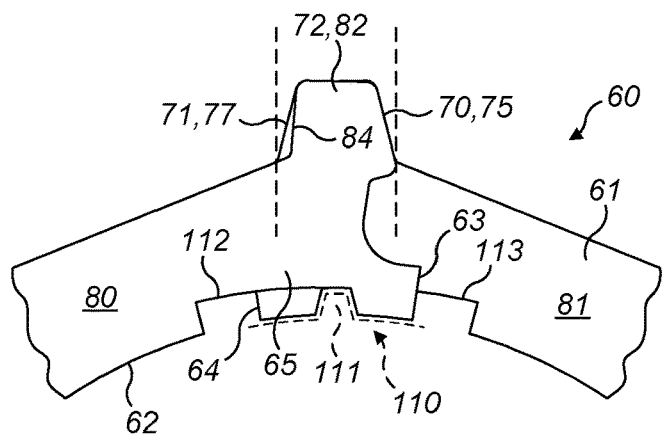

The locking ring 61 has an inner circumference 62 and is adjustable between a locked configuration (illustrated in FIGS. 2 to 6, 11 and 12) and an unlocked configuration (illustrated in FIG. 14). In the locked configuration the locking ring 61 is for maintaining the coupling assembly 12 in the coupled configuration, preferably by holding the first and second coupling 20, 40 together, and the inner circumference 62 of the locking ring 61 is less than in the unlocked configuration. In the unlocked configuration the locking ring 61 is for allowing the coupling assembly 12 to be adjusted to the uncoupled configuration, particularly by allowing separation of the first and second coupling 20, 40.

Figure 10:
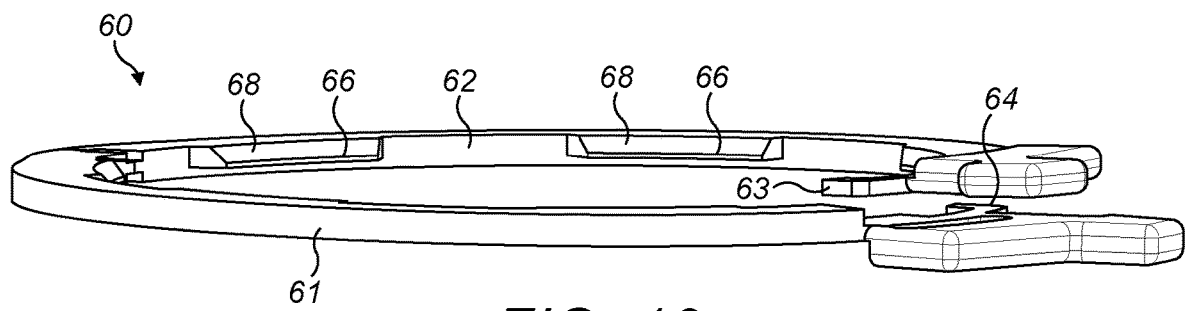
FIG. 10 is a perspective view of the top of the locking arrangement of the coupling assembly of FIG. 1 in an axially flexed arrangement to show a split of the locking arrangement.

The locking ring 61 may be springy, preferably in at least the radial direction 16, and may be resiliently biased to reduce the inner circumference 62 and return from the unlocked configuration to the locked configuration. As in the illustrated embodiment the locking ring 61 may be flexible and substantially non-extendable along its length. The inner circumference 62 may be adjustable by virtue of the locking ring 61 comprising first and second locking ring ends 63, 64 moveable relative to one another between the locked and unlocked configurations. As best shown in FIG. 10 the locking ring 61 may be split such that the first and second locking ring ends 63, 64 are free ends.

Figure 12:
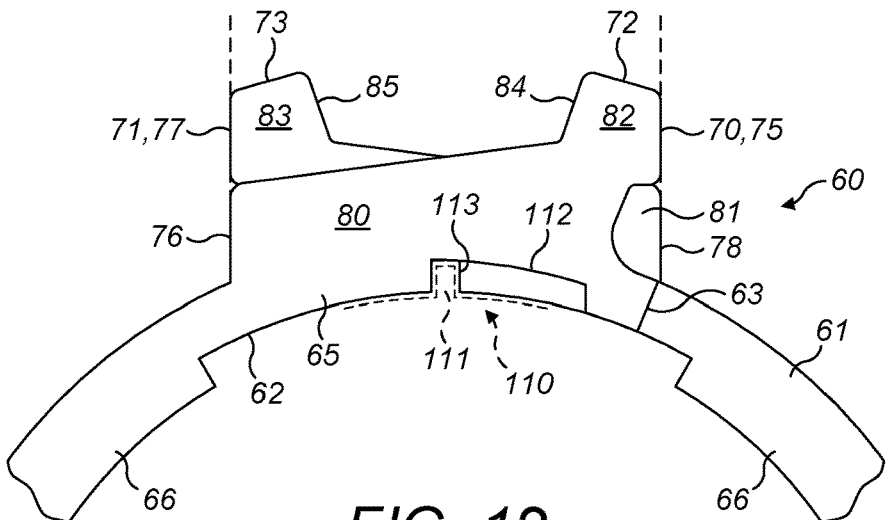
FIGS. 12 TO 14 are a front views of a top of a further embodiment of a locking arrangement of a coupling assembly in accordance with the present disclosure in a locked, intermediate and unlocked configuration respectively and showing, in particular, features in broken lines that would otherwise be hidden from view.
Figure 13:
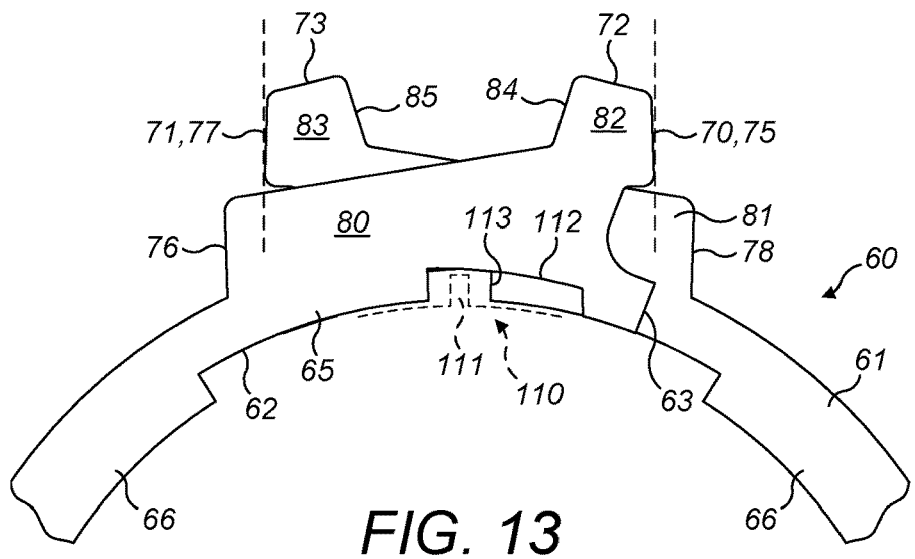

The length of the locking ring 61, which may be the distance around the locking ring 61 between the first and second locking ring ends 63, 64, may be greater than the inner circumference 62 in the locked configuration. The locking ring 61 may therefore comprise an overlapping section 65 over which the locking ring 61 overlaps itself. The overlapping section 65 may extend between the first and second locking ring ends 63, 64 and may decrease in area as the inner circumference 62 increases (as shown in FIGS. 12 to 14).

The locking ring 61 may comprise at least one locking tab 66 extending radially inwardly for selectively maintaining the coupling assembly 12 in the coupled configuration when the locking ring 61 is in the locked configuration. The locking ring 61 may be configured such that its inner circumference 62 is increasable sufficiently for the at least one locking tab 66 to be moved out of engagement with the second coupling 40 such that the first and second couplings 20, 40 can be uncoupled. A plurality of locking tabs 66, preferably at least four and optionally six as illustrated, may be disposed around the inner circumference 62 of the locking ring 61.

The at least one locking tab 66 may be configured to engage with the second coupling 40 when in the coupled and locked configurations to maintain the first and second couplings 20, 40 in the coupled configuration. The at least one locking tab 66 may be configured to at least partially overlap the second coupling outer flange 43 and may extend into the first coupling channel 22 when in the coupled and locked configurations. The at least one locking tab 66 may selectively lock the second coupling outer flange 43 between itself and the first coupling 20, particularly the first coupling flange 24 thereof. The at least one first coupling opening 30 may be configured to receive the at least one locking tab 66. The at least one locking tab 66 may be configured to extend through the at least one first coupling opening 30 in the locked and coupled configuration.

The or each locking tab 66 may comprise a locking tab flat edge 67 for abutting the second coupling flat edge 45 in the locked and coupled configurations and may comprise a locking tab chamfered edge 68 for sliding against the second coupling chamfered edge 44 during coupling. During insertion of the second coupling 40 into the first coupling channel 22 the locking tab chamfered edge 68 may abut and slide against the second coupling chamfered edge 44, which may push the least one locking tab 66 radially outwardly such that the inner circumference 62 of the locking ring 61 increases. The second coupling outer flange 43 may then pass into the first coupling channel 22 and the at least one locking tab 66 may then return to its locked configuration, in which the locking tab flat edge 67 may abut the second coupling flat edge 45.

The locking arrangement 60 comprises first and second grips 70, 71 mounted to the locking ring 61 for adjusting the inner circumference 62. The first and second grips 70, 71 are positioned about the locking ring 61 to be moveable towards one another to increase the inner circumference 62 and adjust the locking ring 61 from the locked configuration to the unlocked configuration. Such adjustment or movement may be initiated by the user pinching the first and second grips 70, 71 together. The locking ring 61 may be resiliently biased to move the first and second grips 70, 71 away from each other such that the locking ring 61 is adjusted from the locked configuration to the unlocked configuration. In particular, the user may not need to apply a force to allow them to move apart and can simply release them.

The first and second grips 70, 71 may be separated from one another around the length of the locking ring 61. The distance between the first and second grips 70, 71 around the length of the locking ring 61 may be greater than the inner circumference 62 in the locked configuration. Thus when they are pushed together they may increase the inner circumference 62. The first and second grips 70, 71 may be located at the top of the coupling assembly 12 and ostomy appliance 10 when in use such that they are easily accessible.

The locking arrangement 60 may further comprise first and second pinch tabs 72, 73 extending, preferably radially outwardly, from the locking ring 61 and forming the first and second grips 70, 71 respectively. The first and second pinch tabs 72, 73 may slide adjacent to one another when the locking ring 61 is adjusted between the locked and unlocked configurations.

Figure 11:
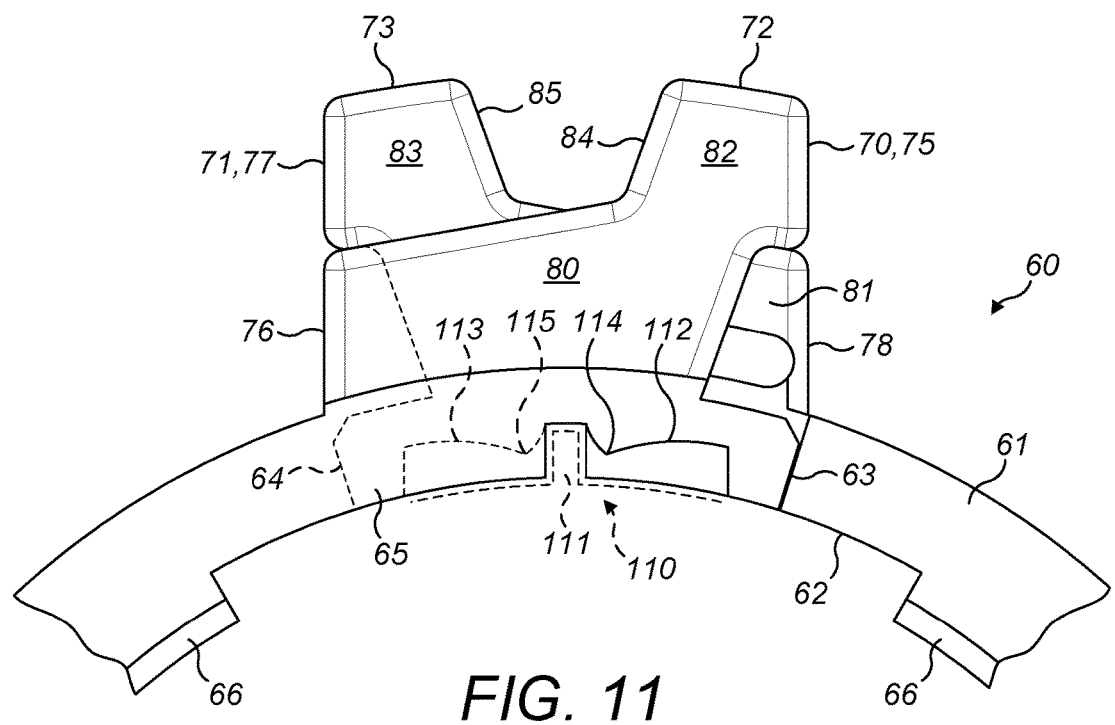
FIG. 11 is a front view of the top of the locking arrangement of the coupling assembly of FIG. 1 showing, in particular, features in broken lines that would otherwise be hidden from view.

FIG. 11 illustrates the first and second pinch tabs 72, 73 of the embodiments of FIGS. 2 to 10 in further detail in the locked configuration. FIGS. 12 to 14 illustrate a further embodiment of the first and second pinch tabs 72, 73 moving from the locked configuration (FIG. 12) to the unlocked configuration (FIG. 14) through an intermediate configuration (FIG. 13). The same reference numerals have been used to show common features and the principle of the movement of the first and second pinch tabs 72, 73 illustrated in FIGS. 12 to 14 equally applies to the embodiment of FIGS. 2 to 11.

The first pinch tab 72 may extend around the locking ring 61 between a first tab distal end 75 and a first tab proximal end 76. The second pinch tab 73 may extend around the locking ring 61 between a second tab distal end 77 and a second tab proximal end 78. The first and second tab distal ends 75, 77 may form the first and second grips 70, 71 respectively. In the locked configuration the first and second tab distal ends 75, 77 may be substantially aligned with the second and first tab proximal ends 78, 76 respectively, as illustrated in FIGS. 2 to 4, 6, 11 and 12. The alignment may be by virtue of the first and second tab distal ends 75, 77 and second and first tab proximal ends 78, 76 being adjacent to but separated along the radial direction 16. As a result, the user may be able to determine that the locking arrangement 60 is in the locked configuration by confirming this alignment by touch.

The first and second pinch tabs 72, 73 may comprise first and second tab proximal portions 80, 81 respectively, which may be adjacent to the locking ring 61 and may form the first and second tab proximal ends 76, 78. The first and second pinch tabs 72, 73 may comprise first and second tab distal portions 82, 83 respectively, which may extend radially outwardly from the first and second tab proximal portions 80, 81 and may form the first and second tab distal ends 75, 77. The first and second tab distal portions 82, 83 may extend circumferentially around the locking ring 61 from the first and second tab distal ends 75, 77 to first and second tab inner edges 84, 85. In the unlocked configuration the first and second tab distal ends 75, 77 may be substantially aligned with the second and first tab inner edges 85, 84 respectively, as illustrated in FIG. 14. The alignment may be by virtue of the second tab distal ends 75, 77 and second and first tab inner edges 85, 84 being adjacent but separated along the axial direction 17. As a result, the user may be able to determine that the locking arrangement 60 is in the unlocked configuration by confirming this alignment by touch.

When the first and second pinch tabs 72, 73 are between the locked and unlocked configurations, as illustrated in FIG. 13, the first and second tab distal ends 75, 77 may not be aligned axially or radially with the second and first tab inner edges 85, 84 or the second and first tab proximal ends 78, 76 respectively. The user therefore may be able to detect the lack of alignment by touch and move the first and second pinch tabs 72, 73 to the locked or unlocked configuration as required.

The coupling assembly 12 may comprise a first and/or second grip constraining arrangement 110 configured to constrain radial and/or circumferential movement of the first and second grips 70, 71 when the locking ring 61 is adjusted between the locked and unlocked configurations. Radial constraint may ensure that the first and second grips 70, 71 are easy to grip by not moving radially during pinching. Circumferential constraint may ensure that the first and second grips 70, 71 cannot be pushed so far that the locking ring 61 disengages from the first coupling 20.

Figure 6:
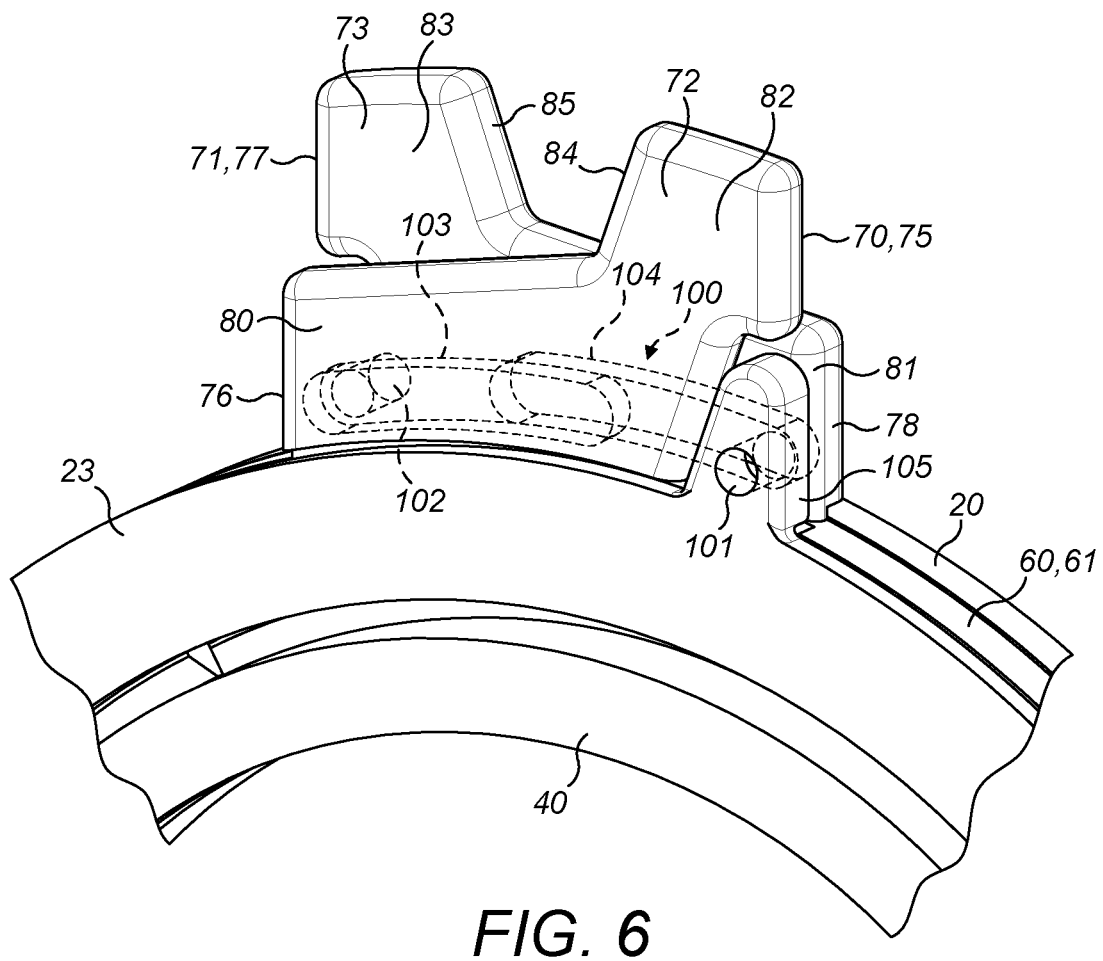
FIG. 6 is a perspective view of a top portion of the coupling assembly of FIG. 1 showing, in particular, features in broken lines which would otherwise be hidden from view.

A particularly suitable embodiment of a first grip constraining arrangement 100 for constraining radial and circumferential movement of the first and second grips 70, 71 is illustrated in FIG. 6 with the use of broken lines. The first grip constraining arrangement 100 may comprise at least one constraining pin 101, 102, which may extend axially, slidably mounted in at least one constraining slot 103, 104, which may extend circumferentially. The at least one constraining slot 103, 104 may be formed in at least one of the locking ring 61, first pinch tab 72 and second pinch tab 73 and the at least one constraining pin 101, 102 may be attached to the first coupling 20 or vice-versa. As illustrated, the first and second pinch tabs 72, 73 may comprise first and second constraining slots 103, 104 respectively facing axially inwardly towards the second and first pinch tabs 73, 72 respectively. First and second constraining pins 101, 102 may be mounted to the first coupling 20, particularly to constraining pin mounts 105, 106 of the first coupling 20 such that they cannot move relative to the first coupling 20, and may be slidably mounted in the second and first constraining slots 104, 103 respectively.

During movement of the first and second grips 70, 71 between the locked and unlocked configurations the first and second constraining slots 103, 104 may slide past one another and the first and second constraining pins 101, 102 may slide in the first and second constraining slots 103, 104. The breadth of the first and second constraining slots 103, 104 is similar to the diameter of the first and second constraining pins 101, 102 such that radial movement of the first and second grips 70, 71 is substantially constrained. In addition, the length of the first and second constraining slots 103, 104 is such that the first and second constraining pins 101, 102 abut the ends of the first and second constraining slots 103, 104 in the unlocked configuration. Thus the first and second grips 70, 71 are constrained or prevented from moving beyond their unlocked configuration in the circumferential direction 15.

Particularly suitable embodiments of a second grip constraining arrangement 110 for constraining circumferential movement of the first and second grips 70, 71 are illustrated in FIGS. 8 and 11 to 14 (with the use of broken lines in FIG. 11). The second grip constraining arrangement 110 may comprise a radially extending constraining protrusion 111 mounted in at least one radially extending constraining recess 112, 113. The first coupling 20 may comprise the constraining protrusion 111 and the locking ring 61 may comprise the at least one constraining recess 112, 113 as illustrated or vice-versa. The constraining protrusion 111 (shown in broken lines in FIGS. 11 to 14) may extend radially outwardly from the first coupling slot base 28 partially into the first coupling slot 25. The locking ring 61 may comprise first and second constraining recesses 112, 113 extending radially outwardly from the inner circumference 62 and located towards its first and second locking ring ends 63, 64 respectively.

As illustrated in FIGS. 12 to 14, the constraining protrusion 111 may remain in the first and second constraining recesses 112, 113 as the first and second grips 70, 71 are moved between the locked and unlocked configurations. The lengths and positions of the first and second constraining recesses 112, 113 may be configured such that the constraining protrusion 111 is at their ends (see FIG. 14) in the unlocked configuration. Thus the first and second grips 70, 71 are constrained or prevented from moving beyond their unlocked configuration in the circumferential direction 15.

As illustrated in FIG. 11, in an embodiment the first and/or second constraining recess 112, 113 may be shaped to provide an initial resistance to moving the first and second grips 70, 71 out of the locked configuration. In particular, the breadth of the first and/or second constraining recess 112, 113 may be reduced at a constriction 114, 115 adjacent to the location of the constraining protrusion 111 in the locked configuration. The first and/or second constraining recess 112, 113 and constraining protrusion 111 must be pushed through this constriction 114, 115 to move them from the locked configuration. As a result, tactile and/or audible feedback of such unlocking may be detected by the user.

The coupling assembly 12 may comprise a centring arrangement 120 configured to constrain and prevent circumferential movement of at least a portion of the locking ring 61 when the locking ring 61 is adjusted between the locked and unlocked configurations. As a result, when the inner circumference 62 is increased, the movement of the first and second grips 70, 71 is translated into a radially outward movement of the locking ring 61 at the centring arrangement 120. Thus symmetrical retraction of the at least one locking tab 66 away from the second coupling 40 can be achieved. The centring arrangement 120 is preferably located at the opposite region of the coupling assembly 12 to the first and second grips 70, 71 and may thus be in the lower portion of the coupling assembly 12 as illustrated.

Figure 4:
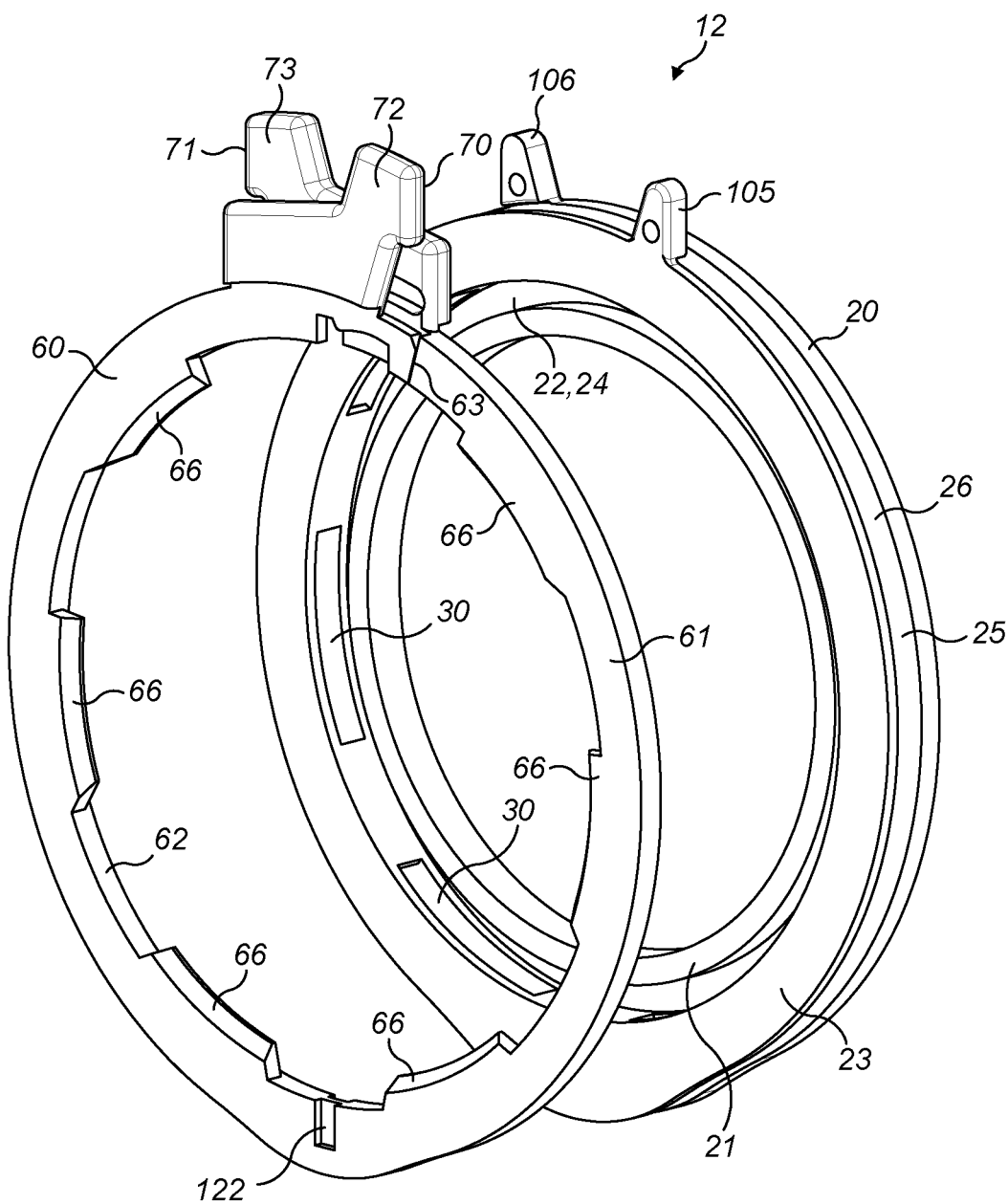
FIG. 4 is a perspective exploded view of a first coupling and a locking arrangement of the coupling assembly of FIG. 1.
Figure 5:
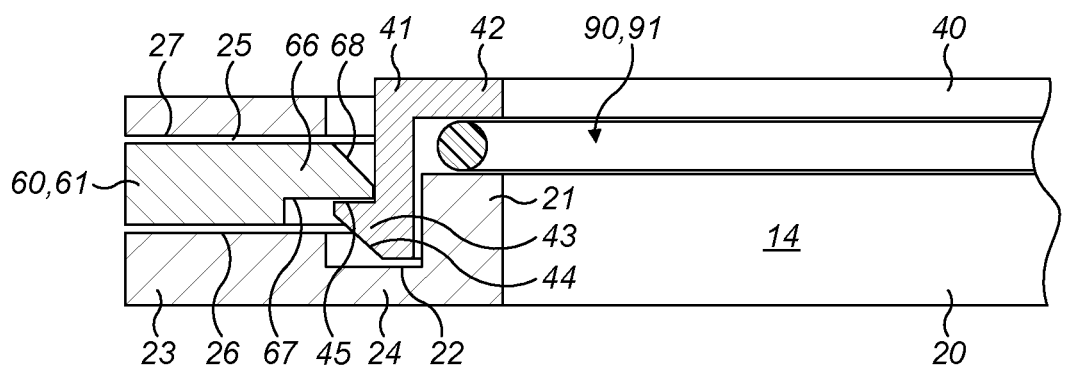
FIG. 5 is a cross-sectional side view across the breadth of the coupling assembly of FIG. 1.
Figure 7:
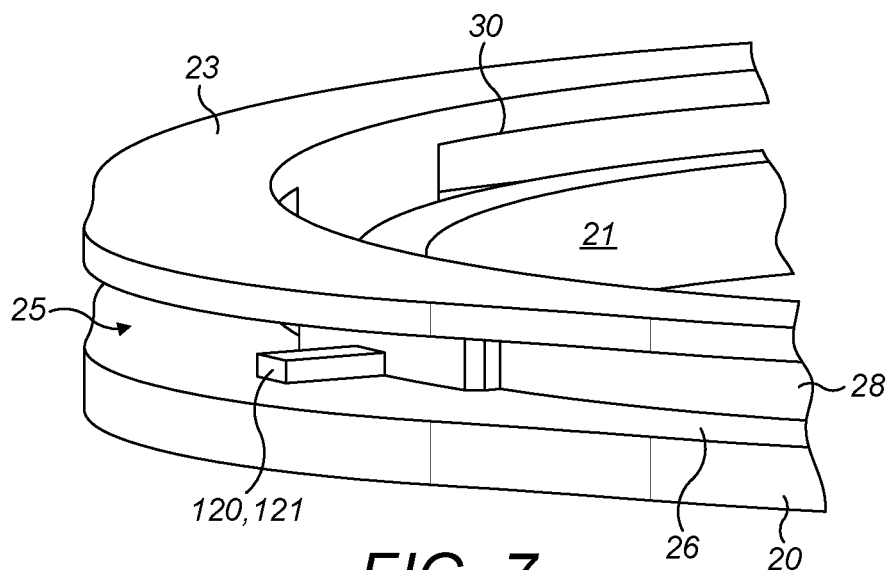
FIG. 7 is a perspective view of a bottom of the first coupling of the coupling assembly of FIG. 1.
Figure 8:
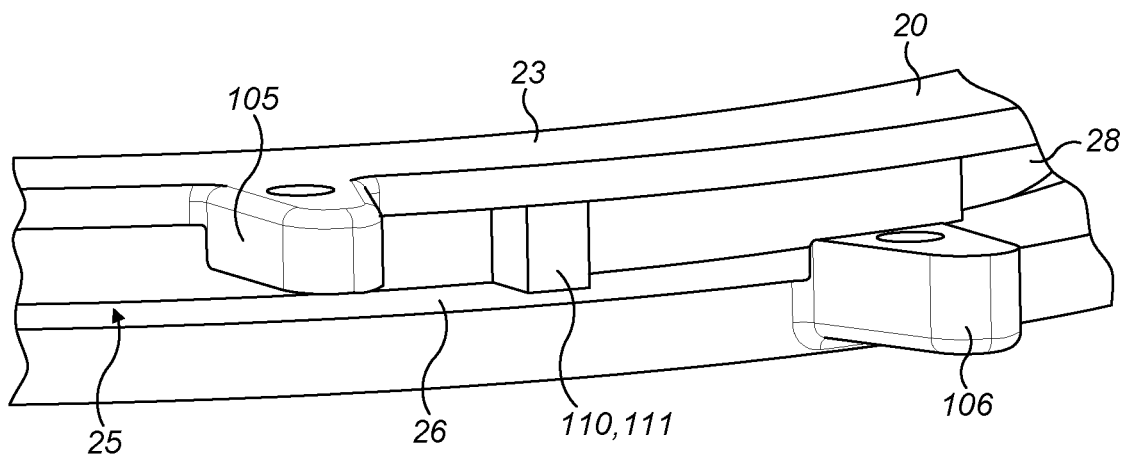
FIG. 8 is a perspective view of a top of the first coupling of the coupling assembly of FIG. 1.

A suitable embodiment is illustrated in FIGS. 4 and 7 and the centring arrangement 120 may comprise at least one centring protrusion 121 mounted in at least one centring recess 122. The first coupling 20 may comprise the at least one centring protrusion 121, which may extend axially, and the locking ring 61 may comprise the at least one centring recess 122, which may extend axially, as illustrated or vice-versa. The centring protrusion 121 may be located in the first coupling slot 25 and extend radially along the first coupling slot wall 26 from the first coupling slot base 28. The at least one centring protrusion 121 may extend from the inner circumference 62 of the locking ring 61. The centring arrangement 120 may be configured such that as the inner circumference 62 increases the locking ring 61 moves away from the first coupling slot base 28 and the at least one centring protrusion 121 and at least one centring recess 122 slide relative to one another. By virtue of the at least one centring protrusion and recess 121, 122 being sufficiently long they may remain engaged in the locked and unlocked configurations.

The first coupling 20, second coupling 40 and locking arrangement 60 may be formed by moulding each component separately and then assembling them together. The sealing arrangement 90 may be moulded with the first and/or second coupling 40 or connected thereto during assembly. The first and second couplings 20, 40 may be relatively rigid and the locking arrangement 60 may be more flexible than the first and second couplings 20, 40.

The first coupling 20, second coupling 40 and/or clamp arrangement 60 may comprise at least one of polyethylene (PE), low density PE (LDPE), high density PE (HDPE), polypropylene homopolymer (PP-H), acrylonitrile butadiene styrene (ABS), an ethylene based octene plastomer (such as Exact® 0230), polypropylene (PP, such asSabic® 58MNK 10), thermoplastic material and the like. In an embodiment the first and second couplings 20, 40 may comprise PE, such as LDPE, and/or the clamp arrangement 60 may comprise PP-H or ABS.

Various alternatives to the embodiments discussed above also fall within the scope of the present disclosure. The locking ring 61 may be elasticated or comprise a cable or the like. The locking ring 61 may not be split and instead a flexible joint, catch or the like may be provided between the first and second locking ring ends 63, 64.

The invention claimed is:

1. A coupling assembly for an ostomy appliance comprising a locking arrangement, a first coupling and a second coupling, wherein the locking arrangement comprises:
a locking ring, mounted to the first coupling, forming an inner circumference and being adjustable between locked and unlocked configurations, wherein in the locked configuration the locking ring is for maintaining a coupled configuration between the first coupling and the second coupling and the inner circumference of the locking ring is less than in the unlocked configuration;
first and second grips mounted to the locking ring, wherein the first and second grips are positioned about the locking ring to be moveable towards one another to increase the inner circumference and adjust the locking ring from the locked configuration to the unlocked configuration;
a first grip constraining arrangement comprising a first constraining slot defined in the locking ring and a corresponding constraining pin extending from the locking ring and at least partially positioned within the first constraining slot; and
a second grip constraining arrangement comprising at least one constraining recess defined in the locking ring and a constraining protrusion extending from the first coupling, the constraining protrusion configured to be at least partially positioned in the at least one constraining recess;
wherein the first grip constraining arrangement and the second grip constraining arrangement are configured to constrain radial and circumferential movement of the first and second grips when the locking ring is adjusted between the locked and unlocked configurations.

2. The coupling assembly as claimed in claim 1 wherein the locking ring comprises first and second locking ring ends moveable relative to one another between the locked and unlocked configurations.

3. The coupling assembly as claimed in claim 2 wherein the locking ring extends around a length that is greater than the inner circumference in the locked configuration.

4. The coupling assembly of claim 1 further comprising first and second pinch tabs extending from the locking ring and comprising the first and second grips respectively, wherein the first pinch tab extends around the locking ring between a first tab distal end and a first tab proximal end, the second pinch tab extends around the locking ring between a second tab distal end and a second tab proximal end and the first and second tab distal ends form the first and second grips.

5. The coupling assembly as claimed in claim 4 wherein the first and second pinch tabs comprise first and second tab proximal portions adjacent to the locking ring forming the first and second tab proximal ends and first and second tab distal portions extending radially outwardly from the first and second tab proximal portions forming the first and second tab distal ends.

6. The coupling assembly as claimed in claim 5 wherein the first and second tab distal portions extend around the locking ring between the first and second tab distal ends and first and second tab inner edges, wherein in the unlocked configuration the first and second tab distal ends are aligned with the second and first tab inner edges respectively.

7. The coupling assembly as claimed in claim 1 comprising first and second pinch tabs that slide adjacent to one another when the locking ring is adjusted between the locked and unlocked configurations.

8. The coupling assembly as claimed in claim 1:
wherein the locking ring comprises at least one locking tab extending inwardly around the inner circumference for maintaining the coupling assembly in the coupled configuration when the locking ring is in the locked configuration;
wherein the locking ring is mounted to the first coupling and the at least one locking tab is configured to engage with the second coupling when in the coupled and locked configurations to maintain the first and second couplings in the coupled configuration;
wherein the first coupling comprises at least one first coupling opening, the at least one locking tab being configured to engage the second coupling through the at least one first coupling opening when in the coupled and locked configurations to maintain the first and second couplings in the coupled configuration.

9. The coupling assembly as claimed in claim 8 wherein the second coupling comprises a second coupling outer flange, the at least one locking tab being configured to at least partially overlap the second coupling outer flange when in the coupled and locked configurations to maintain the first and second couplings in the coupled configuration.

10. The coupling assembly as claimed in claim 1 further comprising a first and second grip constraining arrangement configured to constrain radial and/or circumferential movement of the first and second grips when the locking ring is adjusted between the locked and unlocked configurations.

11. The coupling assembly as claimed in claim 1 further comprising a centring arrangement configured to constrain circumferential movement of at least a portion of the locking ring when the locking ring is adjusted between the locked and unlocked configurations.

12. A coupling assembly for an ostomy appliance, comprising:
a locking arrangement, a first coupling and a second coupling, wherein the locking arrangement comprises:
a locking ring, mounted to the first or second coupling, forming an inner circumference and being adjustable between locked and unlocked configurations;
first and second grips mounted to the locking ring and being moveable towards one another to increase the inner circumference and adjust the locking ring from the locked configuration to the unlocked configuration;
a first grip constraining arrangement comprising a first constraining slot defined in the locking ring and a corresponding constraining pin;
a second grip constraining arrangement comprising first and second constraining recesses extending radially outwardly from the inner circumference of the locking ring and located towards a first and second locking ring ends of the locking ring respectively and
a radially extending constraining protrusion extending from the first coupling and mounted in at least one of the first and second constraining recess;
wherein, the constraining protrusion remains in the first and second constraining recesses as the first and second grips are moved between the locked and unlocked configurations;
wherein the first grip constraining arrangement and the second grip constraining arrangement are configured to constrain radial and circumferential movement of the first and second grips when the locking ring is adjusted between the locked and unlocked configurations.

13. The coupling assembly as claimed in claim 12, further comprising:
   a sealing arrangement extending around a coupling aperture, the sealing arrangement being located between the first and second couplings in the coupled configuration;
   wherein, in the coupled configuration the sealing arrangement is compressed along the axial direction to form a seal between the first and second couplings and the sealing arrangement is located adjacent to and at least partially bounds the coupling aperture;
   wherein the first coupling comprises a first coupling inner wall and a first coupling channel extending around the first coupling inner wall and the second coupling comprises a second coupling wall and a second coupling inner flange extending radially inwardly towards the coupling aperture from the second coupling wall;
   wherein in the coupled configuration the second coupling wall extends into the first coupling channel, the second coupling inner flange extends over the first coupling inner wall and the sealing arrangement is formed between the second coupling inner flange and first coupling inner wall.

14. The coupling assembly as claimed in claim 13 wherein the sealing arrangement comprises a seal element that is mounted between the second coupling inner flange and first coupling inner wall.

15. The coupling assembly as claimed in claim 14 wherein the seal element is attached to the second coupling.

16. The coupling assembly as claimed in claim 13 wherein the second coupling comprises a second coupling outer flange extending radially outwardly away from the coupling aperture from the second coupling wall and in the coupled configuration the second coupling outer flange extends radially outwardly in the first coupling channel.

17. The coupling assembly as claimed in claim 16 wherein the locking ring comprises at least one locking tab extending radially inwardly towards the coupling aperture for selectively maintaining the coupling assembly in the coupled configuration, wherein the at least one locking tab is configured to selectively overlap the second coupling outer flange to hold the first and second coupling in the coupled configuration.

18. The coupling assembly as claimed in 17 wherein a first coupling outer wall comprises at least one first coupling opening for receiving the at least one locking tab such that the at least one locking tab is configured to extend through the at least one first coupling opening and over the second coupling outer flange in the coupled configuration.

19. The coupling assembly of claim 12, wherein the lengths and positions of the first and second constraining recesses are configured such that the constraining protrusion is at end of each of the first and second constraining recesses in the unlocked configuration and the first and second grips are prevented from moving beyond their unlocked configuration in a circumferential direction.

20. The coupling assembly of claim 12, wherein at least one of the first and second constraining recess define a constriction adjacent to the location of the constraining protrusion in the locked configuration, wherein the protrusion must be pushed through the constriction to move the first and second constraining recess between locked and unlocked configurations.

\* \* \* \* \*